(12) United States Patent
Abrahamson

(10) Patent No.: US 10,249,180 B2
(45) Date of Patent: Apr. 2, 2019

(54) IMPLANTABLE MEDICAL DEVICE ADAPTED FOR RADIO FREQUENCY TELEMETRY WITH FREQUENCY HOPPING

(71) Applicant: ST. JUDE MEDICAL AB, Jarfalla (SE)

(72) Inventor: Hans Abrahamson, Stockholm (SE)

(73) Assignee: ST. JUDE MEDICAL AB (SE)

( * ) Notice: Subject to any disclaimer, the term of this patent is extended or adjusted under 35 U.S.C. 154(b) by 0 days.

(21) Appl. No.: 15/644,499

(22) Filed: Jul. 7, 2017

(65) Prior Publication Data

US 2017/0309166 A1    Oct. 26, 2017

Related U.S. Application Data

(62) Division of application No. 13/885,264, filed as application No. PCT/EP2010/068124 on Nov. 24, 2010, now Pat. No. 9,704,385.

(51) Int. Cl.
  *G08C 17/02* (2006.01)
  *A61N 1/372* (2006.01)
  *H04B 1/713* (2011.01)

(52) U.S. Cl.
  CPC ......... *G08C 17/02* (2013.01); *A61N 1/37223* (2013.01); *A61N 1/37252* (2013.01); *H04B 1/713* (2013.01)

(58) Field of Classification Search
  CPC . G08C 17/02; A61N 1/37223–1/37276; A61B 5/0031; H01Q 1/22; H04B 1/713
  See application file for complete search history.

(56) References Cited

U.S. PATENT DOCUMENTS

| | | | | | |
|---|---|---|---|---|---|
| 5,111,535 | A | * | 5/1992 | Tokunaga | H04W 36/30 455/525 |
| 5,734,982 | A | * | 3/1998 | Endo | H04W 84/14 455/11.1 |
| 6,456,256 | B1 | * | 9/2002 | Amundson | A61N 1/37229 128/903 |
| 6,535,766 | B1 | * | 3/2003 | Thompson | A61N 1/025 607/32 |
| 2002/0183806 | A1 | * | 12/2002 | Abrahamson | A61N 1/37276 607/60 |
| 2003/0025645 | A1 | * | 2/2003 | Amundson | A61N 1/37229 343/873 |
| 2004/0027306 | A1 | * | 2/2004 | Amundson | A61N 1/37229 343/873 |
| 2005/0288738 | A1 | * | 12/2005 | Bange | A61N 1/37223 607/60 |

(Continued)

*Primary Examiner* — Orlando Bousono

(57) ABSTRACT

An implantable medical device has a broadband RF receiver operating within an RF band and having stored information of a characteristic receiver frequency representing the RF within the RF band at which the broadband RF receiver has sufficient receiver sensitivity. The stored information is retrieved in response to a message from an external communication device and is included in a response generated by the implantable medical device and transmitted to the communication device. The information enables the communication device to select its transmission frequency at a subsequent transmission instance to the relevant implantable medical device. The chances of successful reception at the subsequent transmission instance are thereby increased.

5 Claims, 6 Drawing Sheets

(56) References Cited

U.S. PATENT DOCUMENTS

| | | | |
|---|---|---|---|
| 2006/0161222 A1* | 7/2006 | Haubrich | A61B 5/0031 607/60 |
| 2006/0195162 A1* | 8/2006 | Arx | A61N 1/37223 607/60 |
| 2006/0247736 A1* | 11/2006 | Roberts | A61N 1/37223 607/60 |
| 2007/0049992 A1* | 3/2007 | Freeberg | A61N 1/37211 607/60 |
| 2007/0060978 A1* | 3/2007 | Haubrich | A61B 5/0006 607/60 |
| 2007/0100396 A1* | 5/2007 | Freeberg | A61N 1/08 607/60 |
| 2007/0167996 A1* | 7/2007 | Dudding | A61N 1/37276 607/60 |
| 2007/0260293 A1* | 11/2007 | Carpenter | A61N 1/3727 607/60 |
| 2008/0071328 A1* | 3/2008 | Haubrich | A61B 5/0031 607/60 |
| 2008/0228237 A1* | 9/2008 | Bange | A61N 1/37252 607/32 |
| 2009/0132007 A1* | 5/2009 | Snitting | A61N 1/025 607/60 |
| 2009/0182388 A1* | 7/2009 | Von Arx | A61B 5/0031 607/5 |
| 2009/0182426 A1* | 7/2009 | Von Arx | A61B 5/0031 623/11.11 |
| 2010/0049272 A1* | 2/2010 | Ljungstrom | A61N 1/37252 607/32 |
| 2010/0176930 A1* | 7/2010 | Shiotsu | G06K 7/10475 340/10.4 |
| 2011/0066211 A1* | 3/2011 | Von Arx | A61N 1/37223 607/60 |
| 2011/0184491 A1* | 7/2011 | Kivi | A61N 1/37276 607/60 |

* cited by examiner

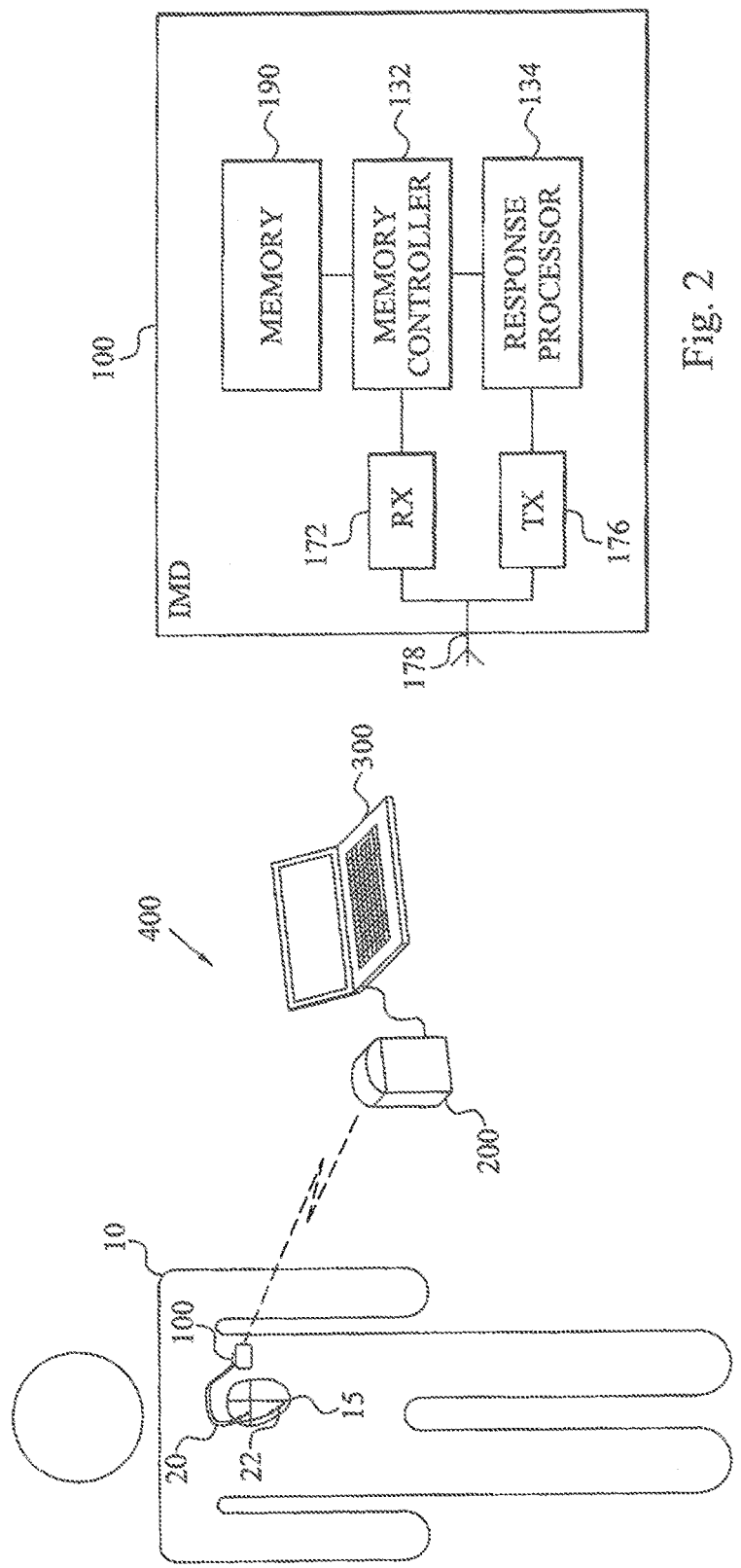

IMPLANTABLE MEDICAL DEVICE ADAPTED FOR RADIO FREQUENCY TELEMETRY WITH FREQUENCY HOPPING

CROSS REFERENCE TO RELATED APPLICATIONS

This application is a division of U.S. patent application Ser. No. 13/885,264, filed May 14, 2013 (now U.S. Pat. No. 9,704,385), which application is a 371 of PCT/EP2010/068124, filed Nov. 24, 2010.

TECHNICAL FIELD

The present invention generally relates to communication with implantable medical devices, and in particular to controlling such communication.

BACKGROUND

The traditional approach of conducting communication with an implantable medical device (IMD) has been through use of inductive telemetry. Currently, the inductive telemetry is replaced by radio frequency (RF) based communication protocols. Usage of RF carriers provides longer communication distances but also introduces new challenges when designing an IMD and its communication circuitry.

One such challenge is that the RF receivers of the IMD should be able to operate within a band of radio frequencies. Broadband RF receivers having optimal receiver frequency within the whole band of radio frequencies are today not practically feasible for IMDs. In clear contrast, practical broadband RF receivers for IMDs generally have varying receiver sensitivities at different radio frequencies within the RF band. A transmitter of a non-implantable communication device can then send at any radio frequency in the band with the potential consequence of the broadband RF receiver missing the communication attempt if the reception condition is poor and the transmission was on a mismatched radio frequency where the broadband RF receiver performs less optimally.

U.S. Pat. No. 7,065,409 discloses an external unit that learns the transmit and receive frequencies for an IMD. The transmit frequency of the IMD is learned by the external unit measuring a difference between the transmit frequency of the IMD and the receive frequency of the external unit. The receive frequency of the IMD is learned by the measured difference between the transmit frequency of the IMD and the receive frequency of the external unit when the implant has a fixed transmit and receive frequency difference. Otherwise, the receive frequency is learned by the IMD measuring the difference between its receive frequency and the transmit frequency of the external unit and by sending an indication of the difference to the external unit through a return signal.

There is, however, still a need for improvements in connection to RF-based communication between an IMD and a non-implantable medical device.

SUMMARY

It is a general objective to improve the communication between an implantable medical device and a non-implantable communication device.

This and other objectives are met by embodiments as disclosed herein.

An aspect of the embodiments defines an implantable medical device (IMD) having a broadband radio frequency (RF) receiver operating within a defined RF band. The receiver characteristics of the RF receiver have been determined in order to identify at least one radio frequency within the RF band at which the broadband RF receiver has sufficient receiver sensitivity. Information of this so-called at least one characteristic receiver frequency is stored in a memory of the IMD. A memory controller is configured to retrieve the information from the memory in response to a message from a non-implantable communication device. A notification of the at least one characteristic receiver frequency is generated based on the retrieved information and is included in a response by a response processor. This response is transmitted by a transmitter of the IMD to the communication device.

Another aspect of the embodiments relates to the non-implantable communication device having a transmitter configured to transmit a first message to the IMD at a radio frequency selected within the RF band at which the broadband RF receiver of the IMD is operating. The communication device comprises a receiver configured to receive a response from the IMD with the notification of the at least one characteristic receiver frequency and an IMD identifier. A memory controller stores the IMD identifier together with information of the at least one characteristic receiver frequency. If the transmitter intends to transmit a second, subsequent message to the IMD identified by the IMD identifier, the memory controller retrieves the stored information from a memory based on the IMD identifier. A transmit controller selects a transmission frequency to be used by the transmitter for the second message based on the retrieved information of the at least one characteristic receiver frequency. The transmitter then transmits the second message on the selected transmission frequency.

The embodiments thereby allow a purposeful selection of transmission frequency at the external communication device to match the receiver characteristics of the broadband RF receiver in the IMD. It is therefore possible to use a transmission frequency that corresponds to the frequency or one of the frequencies within the RF band at which the broadband RF receiver has maximum or at least sufficient receiver sensitivity. The likelihood of successful reception of messages at the IMD is thereby increased as compared to using randomly selected transmission frequencies within the RF band.

A further aspect relates to a method of enabling communication control by receiving a message in the IMD from the communication device. The reception of the message triggers retrieval of information of the at least one characteristic receiver frequency from the IMD memory. A response comprising a notification of the characteristic receiver frequency is generated and transmitted to the communication device.

Yet another aspect of the embodiments defines a communication control method comprising the transmission of a first message to an IMD at a radio frequency selected within a RF band. A response is received from the IMD and comprises an IMD identifier and information of the characteristic receiver frequency of a broadband RF receiver in the IMD. The IMD identifier and the information are stored in a memory. At a subsequent transmission instance the information is retrieved from the memory based on the IMD identifier. A transmission frequency for the subsequent transmission instance is selected based on the retrieved information. A second message is compiled and transmitted to the IMD at the transmission frequency selected based on the retrieved information of the characteristic receiver frequency.

A further aspect of the embodiments defines a method of programming an IMD having a broadband RF receiver configured to operate within a RF band. The method comprises transmitting multiple test messages at different radio frequencies within the RF band to the broadband RF receiver. The receiver sensitivity of the broadband RF receiver is determined for each of the test messages and therefore for each of the tested radio frequencies. A characteristic receiver frequency is identified to correspond to a radio frequency within the RF band at which the broadband RF receiver has at least sufficient receiver sensitivity. A programming command is generated and transmitted to the IMD to trigger the IMD to store information of the identified characteristic receiver frequency in a memory.

BRIEF DESCRIPTION OF THE DRAWINGS

The invention, together with further objects and advantages thereof, may best be understood by making reference to the following description taken together with the accompanying drawings, in which:

FIG. 1 is a schematic overview of an implantable medical device conducting wireless communication with a non-implantable communication device according to an embodiment;

FIG. 2 is a schematic block diagram of an implantable medical device according to an embodiment;

DETAILED DESCRIPTION

Figure 3:
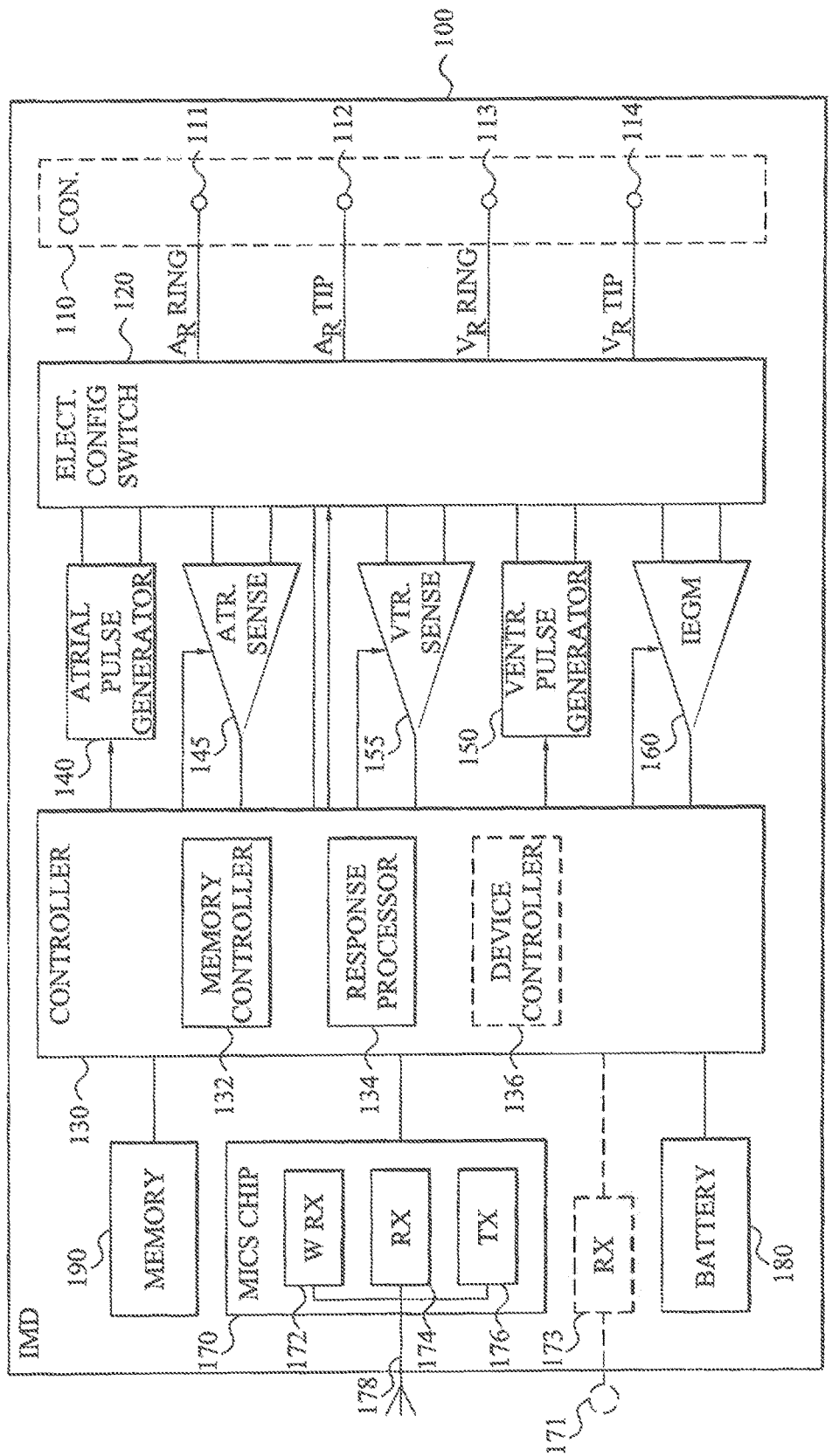
FIG. 3 is a schematic block diagram of an implantable medical device according to another embodiment.

Throughout the drawings, the same reference numbers are used for similar or corresponding elements.

The embodiments generally relate to implantable medical devices and in particular to enabling efficient wireless radio frequency (RF) based communication with such implantable medical devices. There is now a trend within the field of implantable medical devices to replace or at least complement previous inductive communication protocols with RF-based communication counterparts. This development, though, imposes new challenges to the design of the implantable medical devices. For instance, the implantable medical device is battery powered and therefore has limited power supply. Hence, the transmission protocols and equipment of the implantable medical devices need to be designed with regard to these limitations. Interferences and/or poor matching between transmission and reception frequencies can therefore cause disruptions to communication sessions, necessitating new session set-ups and, typically, further drainage of the limited power supply.

Aspects of the embodiments are directed towards solving or at least mitigating these problems by providing a better match between the receiver frequency of an implantable medical device and the transmission frequency employed by an external device communicating with the implantable medical device.

FIG. 1 is a schematic overview of a data communication system according to an embodiment. The data communication system comprises an IMD 100, illustrated as being implanted in a human body 10 in the figure. The IMD 100 of the embodiments can actually be any implantable medical device capable of delivering therapy to an animal, preferably mammalian and more preferably human body 10, and/or capable of recording physiological data and parameters from the body 10. The figure non-limitedly illustrates the IMD 100 as a device monitoring and/or providing therapy to the patient's heart 15 and consequently comprises one or more connectable cardiac leads 20, 22 provided in or in connection to one or more ventricles and/or atriums of the heart 15. The IMD 100 could therefore be a pacemaker, defibrillator or cardioverter. However, the present invention is not limited to cardiac-associated IMDs 100 but may also be practiced with other implantable medical devices 100, such as drug pumps, neurological stimulators, physical signal recorders, oxygen sensors, or the like. The important feature of the IMD 100 is that it contains equipment capable of conducting wireless RF-based communication with an external communication unit 200 of a communication device 400.

The communication unit 200 operates as a base station of the communication device 400 in that it constitutes the interface between the IMD 100 and an external instrument or data processing unit 300, such as a programmer for the IMD 100. This means that the communication unit 200 contains the equipment for effecting the wireless RF-based communication with the IMD 100 on behalf of the data processing unit 300. Data requests from the data processing unit 300 are processed and packed into data packets and transmitted to the IMD 100 by the communication unit 200. Additionally, data packets received from the IMD 100 by the communication unit 200 can be forwarded to the data processing unit 300 for further processing and/or display therein.

The communication unit 200 and the data processing unit 300 can be separate devices as illustrated in FIG. 1, either wired connected or using a wireless connection, such as Bluetooth®, an infrared (IR) connection or an RF connection. In an alternative embodiment, the functionality and equipment of the communication unit 200 and the data processing part of the data processing unit 300 can be housed in a same communication device 400, such as a physician's programmer or workstation. The programmer can additionally comprise or be connected to a display screen for displaying the physiological data collected by the IMD 100 and wirelessly transmitted to the communication unit 200 and processed by the data processor of the programmer. The communication unit 200 and data processing unit 300 could also form a single, portable unit that can be carried by the patient, if desired.

FIG. 2 is a schematic overview of an IMD 100 according to an embodiment. The IMD 100 comprises a broadband RF receiver 172. The RF receiver 172 is configured to operate within a band of radio frequencies and should therefore optimally have high receiver sensitivity within the whole RF band. However, due to manufacturing limitations, component spreading and other effects, the broadband RF receiver 172 will have different receiver sensitivities at the radio frequencies of the RF band. Additionally, different broadband RF receivers manufactured even in the same batch can have substantially differing receiver characteristics.

This means that the broadband RF receiver 172 will have high receiver sensitivity at one or more radio frequencies of the RF band but have comparatively lower and poorer receiver sensitivity at other radio frequencies within the RF band. At these poorer radio frequencies the broadband RF receiver 172 is more sensitive to interferences and the communication link to an external communication device can easily be broken.

According to the embodiments, the receiver characteristics of the broadband RF receiver 172 are characterized and determined in connection with or after manufacture. This means that the receiver sensitivities of the broadband RF receiver 172 at different radio frequencies within the RF band are tested in order to identify at least one characteristic receiver frequency of the broadband RF receiver 172. This characteristic receiver frequency represents a radio frequency within the RF band at which the broadband RF receiver 172 has sufficient receiver sensitivity. Sufficient receiver sensitivity implies that the broadband RF receiver 172 has at least a target or desired receiver sensitivity at the particular radio frequency and therefore is more sensitive to RF signals at that radio frequency as compared to other radio frequencies within the RF band. In a particular embodiment, sufficient receiver sensitivity means that the receiver sensitivity at the particular radio frequency exceeds a defined sensitivity threshold. The defined sensitivity threshold is preferably set to a value corresponding to a case where the broadband RF receiver 172 will, at a sufficient high probability, correctly receive an RF signal transmitted at the particular radio frequency and with a defined transmit power from a transmitter positioned at some target distance from the broadband RF receiver 172. This means that if the selected radio frequency is used there is a high likelihood that the broadband RF receiver 172 will correctly receive the signal from the transmitter even when positioned as far as the target distance from the broadband RF receiver 172. The target distance could then correspond to the typical operating distance between the IMD 100 when implanted and the external communication device, such as from about 0.5 m up to a few meters. The transmit power employed in the test is typically equal to the standardized transmission power employed by external communication devices communicating with IMDs 100.

In a particular embodiment, the at least one characteristic receiver frequency is the radio frequency within the RF band at which the broadband RF receiver 172 has optimal or maximum receiver sensitivity. Thus, the one or multiple radio frequencies within the RF band at which the broadband RF receiver 172 operates best in terms of having maximum receiver sensitivity is or are preferably selected as the characteristic receiver frequency or frequencies of the broadband RF receiver 172.

The receiver sensitivities of the broadband RF receiver 172 are advantageously tested and verified in a test procedure, which will be further described herein. This test procedure can be run in a controlled environment in connection with or following the manufacture of the broadband RF receiver 172. The results from the test procedure are therefore reliable and correctly represent the receiver sensitivities of the broadband RF receiver 172.

Information of the at least one characteristic receiver frequency of the broadband RF receiver 172 is programmed into and stored in a memory 190 of the IMD 100. The IMD 100 also comprises a memory controller 132 that is configured to retrieve the information from the memory 190. In a particular embodiment, the memory controller 132 retrieves the information in response to the reception of a message at the IMD 100 and where the message originates from the non-implantable communication device. The retrieved information of the at least one characteristic receiver frequency is provided to a response processor 134 implemented in the IMD 100. The response processor 134 is configured to generate a response based on the retrieved information. In particular, the response processor 134 includes a notification or information of the at least one characteristic receiver frequency of the broadband RF receiver 172 in the response. The IMD 100 comprises a transmitter 176 connected to the response processor 134 that transmits the response with the notification to the non-implantable communication device using a connected RF antenna 178.

This means that the IMD 100 will inform the non-implantable communication device of the at least one characteristic receiver frequency of its broadband RF receiver 172. The non-implantable communication device can then use that particular radio frequency in the continuing communication session or at another instance as transmission frequency, when the communication device intends to transmit a message to the IMD 100 and the broadband RF receiver 172.

Particular embodiments will now be described in further detail.

FIG. 3 illustrates an embodiment of an IMD 100, exemplified by a device suitable for delivering cardiac therapy to a heart of a subject. The IMD 100 in particular comprises a transmitter 176 connected to an RF antenna 178 and a receiver 174 connected to an RF antenna 178. The transmitter 176 and receiver 174 are employed by the IMD 100 for transmission and reception of data to and from, respectively, the communication device during an established communication session. The transmitter 176 and receiver 174 can be implemented as separate units or can represent the transmitting and receiving branches of a common transceiver. If provided as separate units, they may comprise separate RF antennas or share a common RF antenna 178.

In a preferred embodiment, the IMD 100 additionally comprises a dedicated wakeup receiver 172 that is configured to receive wakeup messages from the communication device. In such a case, the transmitter 176 and receiver 174 could be powered down during an inactive, low-power state, whereas the wakeup receiver 172 is active to receive any wakeup messages. This significantly reduces the power consumption as compared to having the transmitter 176 and the receiver 174 active all time.

The dedicated wakeup receiver 172 can have a separate RF antenna or is connected to the (common) RF antenna 178.

It is generally preferred to have a separate wakeup receiver 172 as illustrated in FIG. 3 since then the communication circuitry utilized for data communication with the communication device can be kept inactivated to thereby only have the wakeup receiver 172 draining a very low amount of power of a battery 180 active to capture wakeup messages.

In a particular embodiment, the wakeup receiver 172 is a broadband RF receiver configured to operate within a band of radio frequencies. In such a case, the wakeup receiver 172 is preferably configured to operate within the Industrial, Scientific and Medical (ISM) band at 2.4000 to 2.4835 GHz. The wakeup receiver 172 should then optimally be configured to cover a band of radio frequencies corresponding to at least 83.5 MHz. In practical implementations, the wakeup receiver 172 will have different receiver sensitivities within this 83.5 MHz band and therefore the receiver characteristics of the wakeup receiver 172 are investigated in order to determine at least one characteristic receiver frequency within the ISM band. Information of the characteristic receiver frequency is stored in the memory 190 in the IMD 100.

The memory controller 132 is advantageously configured to retrieve the information of the characteristic receiver frequency from the memory 190 in response to the wakeup receiver 172 receiving a wakeup call or message from the non-implantable communication device. The response processor 134 generates a wakeup response comprising a notification of the characteristic receiver frequency based on the information retrieved by the memory controller 132. The response processor 134 advantageously generates the response based on or in response to the reception of the wakeup call by the wakeup receiver 172. The transmitter 176 of the IMD 100 then transmits the wakeup response with the notification to the non-implantable communication device.

In an embodiment, the retrieval of the information and the generation of the wakeup response are conducted automatically by the IMD 100 in response to the reception of the wakeup call by the wakeup receiver 172.

In an alternative embodiment, the information is retrieved from the memory 190 in response to an explicit request from the communication device. Such a request is then preferably received by the receiver 174 once a communication session has been set up. The response processor 134 then generates a response message with the notification of the at least one characteristic receiver frequency and the transmitter 176 sends the response message to the communication device.

It could also be possible to conduct an evaluation in the IMD 100 whether there is a need to provide the notification of the at least one characteristic frequency to the communication device. Thus, if the IMD 100 previously already has sent this notification to a communication device and the communication device has stored the notification, there is generally no need to further retransmit the notification once more. In such a case, the message, such as wakeup call, from the communication device comprises a device identifier indicative of the particular communication device. The IMD 100 then comprises an optional device controller 136 configured to investigate whether the IMD 100 and its transmitter 176 have previously sent a previous response comprising the notification to the communication device identified by the device identifier. The device controller 136 compares the received device identifier with previously stored device identifiers in the memory 190. If it was concluded that the received device identifier is found in the memory 190 and the IMD 100 therefore has previously sent the notification to the particular communication device, the device controller 136 preferably controls the memory controller 132 not to retrieve the information of the characteristic receiver frequency from the memory and controls the response processor 134 not to include the notification in the response. However, if the transmitter 176 has previously not sent the notification to the communication device and the device identifier thereby is not found in the memory 190, the device controller 136 preferably controls the memory controller 132 to retrieve the information of the characteristic receiver frequency from the memory 190 and controls the response processor 134 to include the notification in the response. The device controller 136 additionally preferably enters the device identifier in the memory 190 to indicate that the notification of the at least one characteristic receiver frequency has been sent to the particular communication device.

The Information of the at least one characteristic receiver frequency can be programmed into the memory 190 of the IMD 100 using a so-called command receiving receiver 173, 174. In an embodiment, the IMD 100 could have a dedicated inductive receiver 173 with a connected inductive antenna 171. In such a case, a programming command comprising the information is received by the inductive antenna 171 and inductive receiver 173. The programming command controls the memory controller 132 to store the information in the memory 190. Alternatively, the receiver 174 that is activated once the wakeup receiver 172 has received a wakeup call and when the IMD 100 goes from the low-power state to the communication state could be used as command receiving receiver.

The transmitter 176 and the receiver 174 that are preferably inactive during the low-power state and become activated once the wakeup receiver 172 correctly receives a wakeup call can advantageously operate at frequencies within the Medical Implant Communication Service (MICS) radio band at 402 to 405 MHz. Alternatively, the receiver 174 and the transmitter 176 could operate at the ISM radio band at 418 MHz (U.S.), 433.05-434.79 MHz, 868-870 MHz (Europe) or 902-928 MHz (U.S.).

The wakeup receiver 172, the receiver 174 and the transmitter 176 are advantageously implemented together on a communication chip or module, represented by a MICS chip 170 in FIG. 3. MICS chips are currently available from vendors such as Zarlink Semiconductor, such as Zarlink 701xx chips.

In alternative embodiments, the broadband RF receiver does not operate within the 2.4000-2.4835 GHz ISM band but could instead operate in the MICS band or one of the other ISM radio bands currently assigned to implantable and medical devices. It could even be possible to omit the dedicated wakeup receiver 172. The IMD 100 would then comprise a single broadband RF receiver that handles any wakeup signaling and the reception once a communication session has been established.

FIG. 3 additionally depicts various other components of the IMD 100. While a particular multi-chamber device is shown in FIG. 3, it is to be appreciated and understood that this is done merely for illustrative purposes. Thus, the techniques and methods described herein can be implemented in connection with other suitably configured IMDs 100. Accordingly, the person skilled in the art can readily duplicate, eliminate, or disable the appropriate circuitry in any desired combination to provide an IMD 100 capable of treating the appropriate heart chamber(s) with pacing stimulation and optionally also cardioversion and/or defibrillation. The IMD 100 must further not necessarily be a pacemaker or other cardiac stimulating device. In clear contrast, any implantable medical device comprising equipment for enabling RF-based, wireless communication with the communication device is encompassed by the definition of IMD 100 as used herein.

The IMD 100 comprises a housing, often denoted as can or case in the art. The housing can act as return electrode for unipolar leads, which is well known in the art. The IMD 100 also comprises a lead connector 110 having, in this embodiment, a plurality of terminals 111-114. The lead connector 110 is configured to be, during operation in the subject body, electrically connected to at least one cardiac lead, such as a right atrial lead and a right ventricular lead. The lead connector 110 consequently comprises terminals 111, 112 that are electrically connected to matching electrode terminals of an atrial lead when the atrial lead is introduced in the lead connector 110. For instance, one of these terminals 112 can be designed to be connected to a right atrial tip terminal of the atrial lead, which in turn is electrically connected through a conductor running along the lead body to a tip electrode present at the distal end of the atrial lead in the right atrium of the heart. A corresponding terminal 111 is then connected to a right atrial ring terminal of the atrial lead that is electrically connected by another conductor in the lead body to a ring electrode present in connection with the distal part of the atrial lead, though generally distanced somewhat towards the proximal lead end as compared to the tip electrode.

In an alternative implementation, the IMD 100 is not connectable to a right atrial lead but instead to a left atrial lead configured for implantation in the left atrium. A further possibility is to have an IMD 100 with a lead connector 110 having sufficient terminals to allow the IMD 100 to be electrically connectable to both a right atrial lead and a left atrial lead. It is also possible to have a lead connector 110 without any terminals 111, 112 for any atrial leads.

In order to support right chamber sensing and pacing, the lead connector 110 further comprises a right ventricular tip terminal 114 and a right ventricular ring terminal 113, which are adapted for connection to a right ventricular tip electrode and a right ventricular ring electrode, respectively of a right ventricular lead implantable in the right ventricle.

In alternative embodiments, the lead connector 110 is connectable to a left ventricular lead instead of a right ventricular lead or connectable to both a left ventricular lead and a right ventricular lead. A left ventricular lead is typically implanted in the coronary venous system for safety reasons although implantation inside the left ventricle has been proposed in the art. A further possibility is to have a lead connector 110 with terminals 111, 112 that are only connected to one or more atrial leads.

FIG. 3 merely illustrates a typical example of a cardiac lead configuration that can be used in an IMD 100. The teachings of the embodiments are not dependent on a particular lead configuration. In clear contrast, the embodiments can actually be applied to IMDs that do not have any connectable leads at all. The important characteristic is that the IMD 100 comprises a communication circuitry capable of conducting wireless, RF-based communication with the communication device.

The IMD 100 as illustrated in FIG. 3 comprises an atrial pulse generator 140 and a ventricular pulse generator 150 that generate pacing pulses for delivery by the atrial lead(s) and the ventricular lead(s), respectively, preferably through an electrode configuration switch 120.

It is understood that in order to provide stimulation therapy in different heart chambers, the atrial and ventricular pulse generators 140, 150 may include dedicated, independent pulse generators, multiplexed pulse generators, or shared pulse generators. The pulse generators 140, 150 are controlled by a controller 130 via appropriate control signals, respectively, to trigger or inhibit the stimulating pulses.

The controller 130, preferably in the form of a programmable microcontroller, controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 130 is configured to process or monitor input signal as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

The controller 130 further controls the timing of the stimulating pulses, such as pacing rate, atrioventricular interval (AVI), atrial escape interval (AEI) etc. as well as to keep track of the timing of refractory periods, blanking periods, noise detection windows, evoked response windows, alert intervals, marker channel timing, etc.

A preferred electronic configuration switch 120 includes a plurality of switches for connecting the desired terminals 111-114 to the appropriate I/O circuits, thereby providing complete electrode programmability. Accordingly, the electronic configuration switch 120, in response to a control signal from the controller 130, determines the polarity of the stimulating pulses (e.g., unipolar, bipolar, combipolar, etc.) by selectively closing the appropriate combination of switches (not shown) as is known in the art An atrial sensing circuit or detector 145 and a ventricular sensing circuit or detector 155 are also selectively coupled to the atrial lead(s) and the ventricular lead(s), respectively, through the switch 120 for detecting the presence of cardiac activity in the heart chambers. Accordingly, the atrial and ventricular sensing circuits 145, 155 may include dedicated sense amplifiers, multiplexed amplifiers, or shared amplifiers. The switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture Each sensing circuit 145, 155 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 145, 155 are connected to the controller 130, which, in turn, is able to trigger or inhibit the atrial and ventricular pulse generators 140, 150, respectively, in a demand fashion in response to the absence or presence of cardiac activity in the appropriate chambers of the heart Furthermore, the controller 130 is also capable of analyzing information output from the sensing circuits 145, 155 and/or an Intracardiac electrogram (IEGM) acquisition unit 160 to determine or detect whether and to what degree tissue capture has occurred and to program a pulse, or pulse sequence, in response to such determinations. The sensing circuits 145, 155, in turn, receive control signals over signal lines from the controller 130 for purposes of controlling the gain, threshold, polarization charge removal circuitry, and the timing of any blocking circuitry coupled to the inputs of the sensing circuits 145, 155 as is known in the art.

Cardiac signals are also applied to inputs of the IEGM acquisition unit 160. The IEGM acquisition system 160 is configured to acquire intracardiac electrogram signals, convert the raw analog data into a digital signal, and store the digital signals for later processing and/or transmission to the programmer by the transmitter 176. The IEGM acquisition system 160 is coupled to the atrial lead(s) and/or the ventricular lead(s) through the switch 120 to sample cardiac signals across any pair of desired electrodes The controller 130 is further coupled to the memory 190 by a suitable data/address bus, wherein the programmable operating parameters used by the controller 130 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, and time interval between pacing pulse of an applied pacing pulse sequence. The memory 190 could be the same as the memory housing the information of the at least one characteristic receiver frequency or a separate memory A battery 180 is provided in the IMD 100 to generate the operating power for the units of the IMD 100

In an embodiment, the memory controller 132, the response processor 134 and the optional device controller 136 are implemented as parts of the controller 130. In such a case, these units 132, 134, 136 of the controller 130 are implemented as hardware components or as computer program code elements or software code portions stored in the memory 190 and executed by the controller 130.

Figure 4:
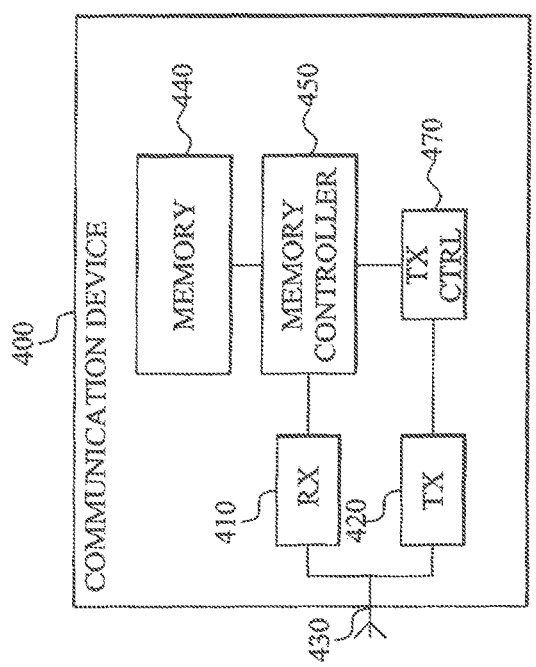
FIG. 4 is a schematic block diagram of a non-implantable communication device according to an embodiment.

FIG. 4 is a schematic block diagram of a non-implantable communication device 400 according to an embodiment. The communication device 400 is configured to conduct wireless communication with an IMD, such as the IMD of FIG. 2 or 3. The communication device 400 comprises a transmitter 420 configured to transmit a first message to the IMD at a radio frequency selected within a band of radio frequencies. The first message could be a first wakeup call, for instance at a frequency within the 2.4000 to 2.4835 GHz ISM band. In an alternative embodiment, the first message could be a request for information of characteristic receiver frequency of a broadband RF receiver in the IMD.

The radio frequency for the first message is preferably selected by a transmit controller 470 of the communication device 400. However, the communication device 400 and the transmit controller 470 do, at this point, not know the receiver sensitivities of the broadband RF receiver and therefore do not know which radio frequency within the RF band that would be optimal from receiver sensitivity point of view. Hence, the radio frequency selected could be randomly selected within the RF band by the transmitter controller 470. Alternatively, the transmitter controller 470 could select the latest radio frequency within the RF band that was used in a previous communication session with an IMD.

The selected radio frequency will therefore most probably not be the best radio frequency for the broadband RF receiver capturing the first message.

The communication device 400 also comprises a receiver 410 connected to an RF antenna 430, either a dedicated RF receiving antenna or a common RF antenna that is connected also to the transmitter 420. In the former case, the transmitter 420 has a dedicated RF transmitting antenna. The receiver 410 is configured to receive a response from the IMD. The response comprises an IMD identifier indicative of the particular IMD and a notification of the at least one characteristic receiver frequency at which the broadband RF receiver of the IMD has sufficient, preferably maximum, receiver sensitivity.

A memory controller 450 is connected to the receiver 410 and a memory 440. The memory controller 450 then retrieves the IMD identifier and the information of the at least one characteristic receiver frequency from the response and stores them in the memory 440.

The next time the communication device 400 intends to send a message to the broadband RF receiver of the IMD, such as a next wakeup message or call, the memory controller 450 retrieves the information from the memory 440 based on the IMD identifier associated with the intended receiving IMD. The retrieved information is provided to the transmitter controller 470 that selects a transmission frequency based on the information. The transmitter controller 470 preferably selects the transmission frequency to be equal to or at least close to one of the at least one characteristic receiver frequency indicated in the retrieved information. The transmitter 420 then transmits the second message to the IMD at the transmission frequency selected by the transmitter controller 470 based on the information retrieved from the memory 440.

Thus, at this second and further transmission occasions the communication device 400 can optimize the transmission frequency to coincide with a radio frequency at which the broadband RF receiver of the IMD has particularly high receiver sensitivity. The chances of successful reception of the message are thereby significantly increased as compared to randomly selecting a transmission frequency within the RF band.

At the first transmission occasion with a particular IMD, the communication device 400 does not have any a priori information of which radio frequency within the particular RF band to use in order increase the chances of successful reception at the IMD. However, once a communication session has been set up, the IMD will notify the communication device 400 of the characteristic receiver frequency. The communication device 400 can then use that frequency for the remainder of the communication session or, if the characteristic receiver frequency is only employed for transmitting wakeup calls, when setting up a next communication session with the same IMD.

In a particular embodiment, the communication device 400 employs frequency hopping when transmitting a wakeup call to an IMD. For instance, the communication device could use a hop sequence that hops between various radio frequencies within the 2.4000 to 2.4835 GHz ISM band. In such a case, the transmitter controller 470 controls the transmitter 420 to apply frequency hopping within the RF band. Once the IMD has notified the communication device 400 of its at least one characteristic receiver frequency, the transmitter controller 470 preferably controls the transmitter 420 to start the frequency hopping sequence at a radio frequency equal or close to the characteristic receiver frequency or corresponding to one such characteristic receiver frequency if the information from the IMD indicates that multiple alternative radio frequencies can be used with sufficient receiver sensitivity.

Figure 5:
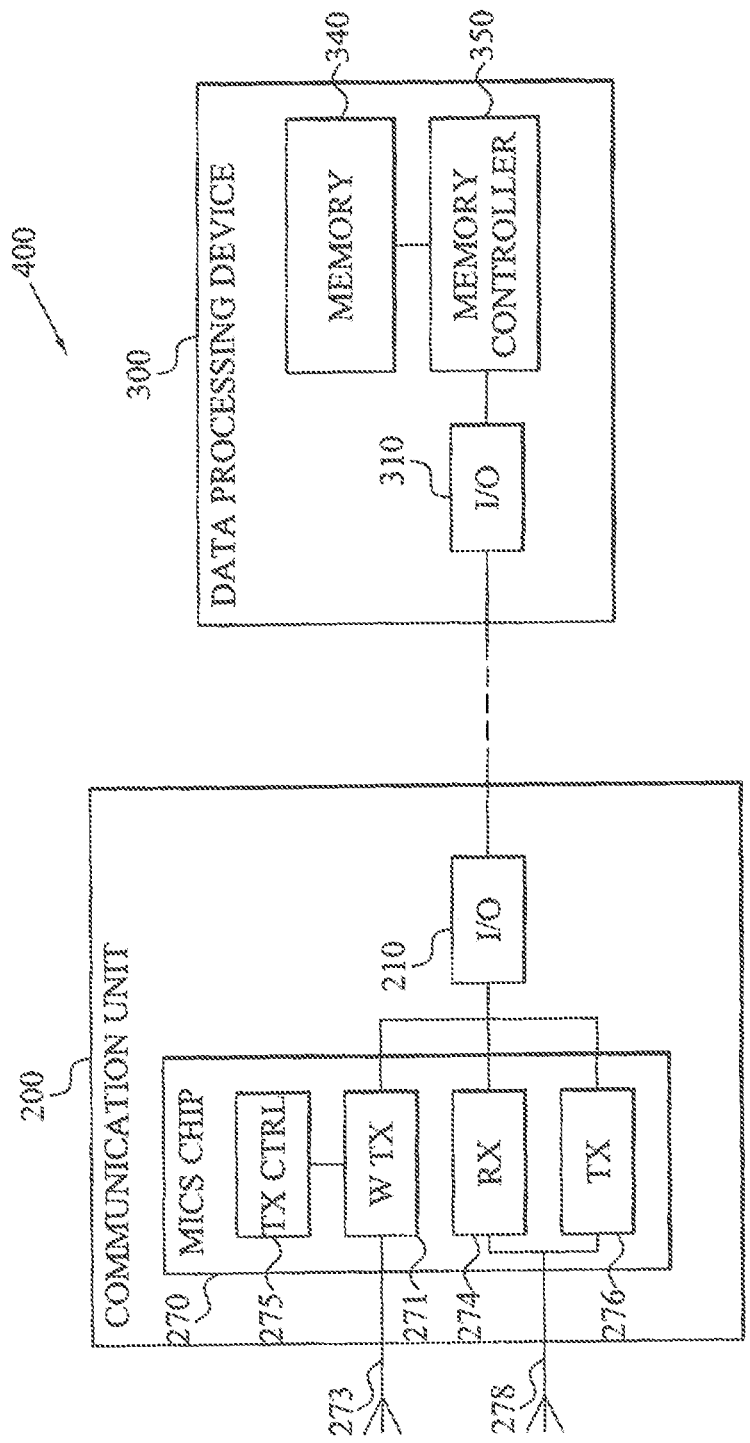
FIG. 5 is a schematic block diagram of a non-implantable communication device according to another embodiment.

The units 410, 420, 450, 470 of the communication device 400 may be implemented or provided as hardware or a combination of hardware and software. In the case of a software-based implementation, a computer program product implementing the units 410, 420, 450, 470 or a part thereof comprises software or a computer program run on a general purpose or specially adapted computer, processor or microprocessor. The software includes computer program code elements or software code portions illustrated in FIG. 4. The program may be stored in whole or part, on or in one or more suitable non-transitory computer readable media or data storage means such as magnetic disks, CD-ROMs, DVD disks, USB memories, hard discs, magneto-optical memory, in RAM or volatile memory, in ROM or flash memory, as firmware, or on a data server FIG. 5 is an illustration of another embodiment of a non-implantable communication device 400 illustrated as being distributed among a communication unit 200 and a data processing device 300. In such a case, the communication unit 200 comprises the equipment required for affecting the wireless RF-based communication between the IMD and the data processing device 300. The communication unit 200 in particular comprises a communication chip 270, such as a MICS chip 270. The communication chip 270 could then include a dedicated wakeup transmitter 271 having a connected RF antenna 273. This wakeup transmitter 271 is configured to transmit wakeup calls to an IMD in order to activate the receiver and transmitter of the MICS chip in the IMD. These wakeup calls are transmitted preferably at a frequency within the 2.4000 to 2.4835 GHz ISM band. The frequency to use within this broadband is selected by a transmitter controller 275. The first time the communication unit 200 wakeups an IMD, the transmitter controller 275 preferably randomly selects a transmission frequency within the ISM band. However, once information of the characteristic receiver frequency of the IMD has been received, the transmitter controller 275 preferably controls the wakeup transmitter 271 to use the characteristic receiver frequency instead of a randomly selected radio frequency.

The communication chip 270 also preferably comprises a receiver 274 and transmitter 276 with dedicated or a common RF antenna 278. The receiver 274 and transmitter 276 are advantageously employed by the communication unit 200 once a communication session has been established and preferably operate within the MICS band or an ISM band within the MHz range.

The communication unit 200 has a wired or wireless connection with the data processing device 300 effected by respective input and output (I/O) units 210, 310. In the case of wired connections, the I/O units 210, 310 represent respective connection ports. In an wireless connection embodiment, the I/O units 210, 310 correspond to the necessary transceiver functionality with optional antennas.

In the illustrated embodiment, the memory controller 350 with connected memory 340 is implemented in the data processing device 300. In such a case, the response message with the information of the at least one characteristic receiver frequency is received by the receiver 274 in the communication unit 200. The information is forwarded by the I/O unit 210 to the I/O unit 310 in the data processing device 300 and the memory controller 350. The memory controller 350 stores the Information together with the IMD identifier in order to be able to identify for which IMD the information is valid. The memory controller 350 then retrieves the information from the memory 340 once the wakeup transmitter 271 is about to transmit a second wakeup call to the IMD. In such a case, the memory controller 350 uses the IMD identifier to locate the relevant information in the memory 340 and forwards the information to the communication chips 270 via the I/O units 210, 310. There the wakeup transmitter 271 can transmit the second wakeup call at a radio frequency selected by the transmitter controller 275 based on the received information and preferably to correspond to one of the at least one characteristic receiver frequency.

Figure 6:
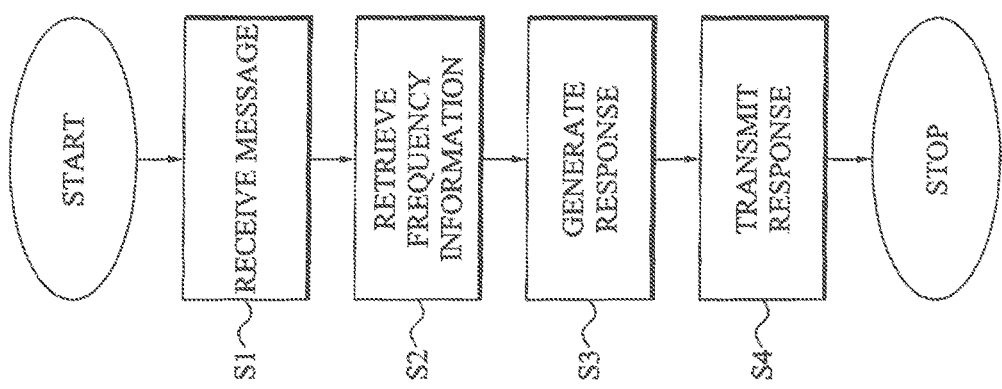
FIG. 6 is a flow diagram illustrating a method of enabling communication control according to an embodiment.

The units 210, 271, 274, 275, 276 of the communication unit 200 and the units 310, 350 of the data processing device 300 may be implemented or provided as hardware or a combination of hardware and software. In the case of a software-based implementation, a computer program product implementing the units or a part thereof comprises software or a computer program run on a general purpose or specially adapted computer, processor or microprocessor. The software includes computer program code elements or software code portions illustrated in FIG. 5. The program may be stored in whole or part, on or in one or more suitable non-transitory computer readable media or data storage means such as magnetic disks, CD-ROMs, DVD disks, USB memories, hard discs, magneto-optical memory, in RAM or volatile memory, in ROM or flash memory, as firmware, or on a data server FIG. 6 is a flow diagram illustrating a method of enabling communication control according to an embodiment. The method starts in step S1, where an IMD having a broadband RF receiver receives a message from a non-implantable communication device. A next step S2 retrieves information of at least one characteristic receiver frequency in response to the received message. The characteristic receiver frequency represents one or more radio frequencies within a defined RF band at which the broadband RF receiver has sufficient, preferably maximum, receiver sensitivity. The following step S3 generates a response based on the information retrieved in step S2 so that the response comprises a notification of the at least one characteristic receiver frequency. The response is transmitter in step S4 to the communication device to inform the device of the particular radio frequency/frequencies at which the broadband RF receiver operates best in terms of receiver sensitivity. The notification in the response thereby enables the communication device to control its selection of transmission frequency for a subsequent message to thereby increase the likelihood of successful reception of the subsequent message at the IMD.

Figure 7:
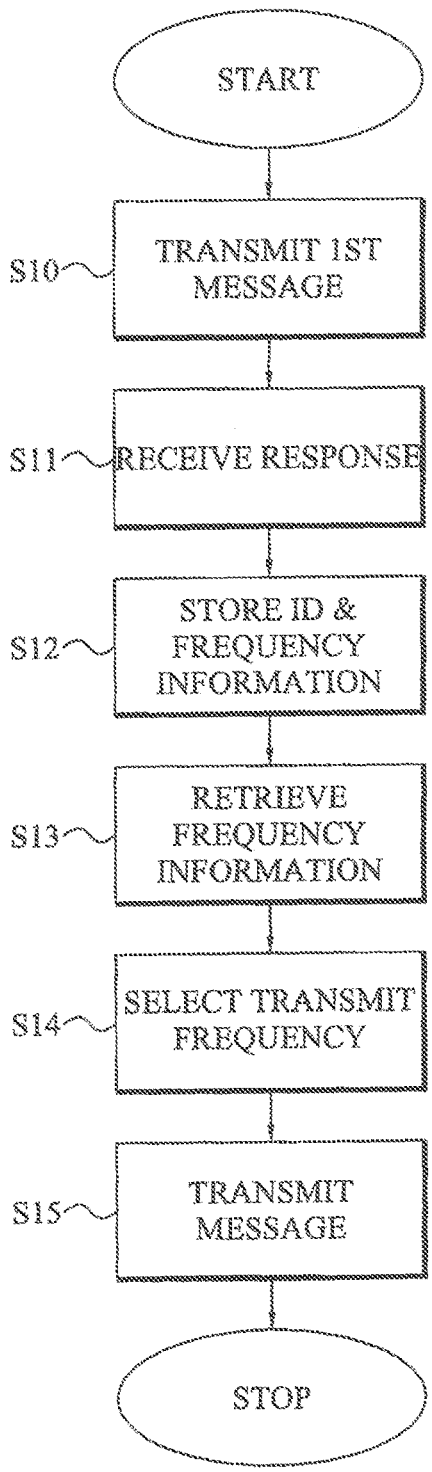
FIG. 7 is a flow diagram of a communication control method according to an embodiment.

FIG. 7 is the corresponding flow diagram of a communication control method. The method starts in step S10 where a first message is transmitted to an IMD at a radio frequency selected within a defined RF band. This radio frequency is selected without any knowledge of the characteristic receiver sensitivity of the broadband RF receiver in the IMD. Hence some other selection criterion is employed and the radio frequency is typically randomly selected within the RF band. A next step S11 receives a response to the message from the IMD. The response comprises an IMD identifier and a notification of the at least one characteristic receiver frequency of the broadband RF receiver. The IMD identifier and the frequency information are stored in step S12 to be used at a subsequent transmission instance. In such a case, the frequency information is retrieved from the memory in step S13 based on the IMD identifier. The retrieved information is employed in step S14 to select transmission frequency for the subsequent transmission instance. A subsequent message is composed and transmitted to the IMD in step S15 at the transmission frequency selected in step S14 based on the frequency information retrieved in step S13

The embodiments inform the non-implantable communication device of a transmission frequency at which the chances of successful reception of a message, such as wakeup call, by the broadband RF receiver in the IMD are increased and typically maximized. The technique is further failure tolerant and does not require extensive measurement or processing in the power-limited IMD. The prior art solution represented by U.S. Pat. No. 7,065,409 is not failure tolerant since it is dependent on an instant measurement between a received signal from the communication device and a tuned receiver frequency, i.e. the centre frequency in the IMD receiver. However, if the IMD receiver is interfered by some external source during this measurement period an erroneous frequency difference will be measured. The system is thereby mistuned.

Figure 8:
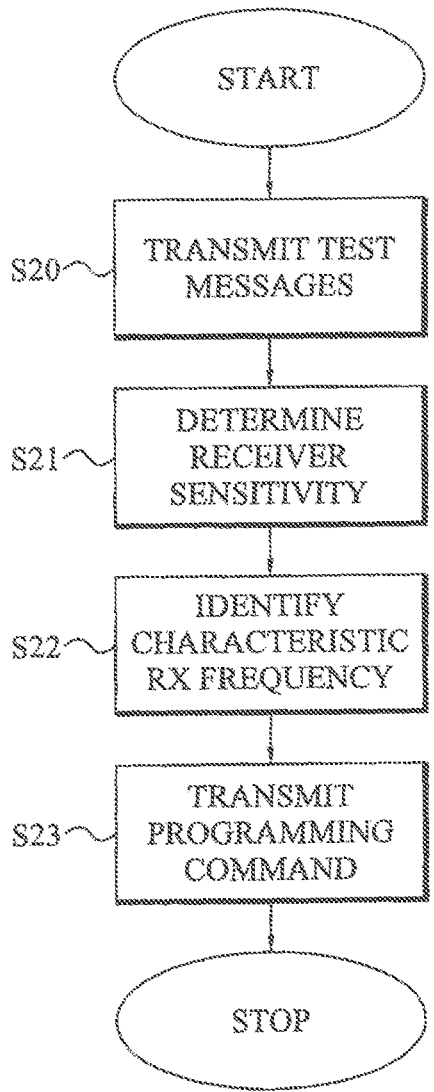
FIG. 8 is a flow diagram of a method of programming an Implantable medical device according to an embodiment.

In contrast, the embodiments store information about preferred receiver frequency or frequencies corresponding to sufficient or maximal receiver sensitivity in the IMD. No frequency differences need to be determined in a potentially interfering environment. The characteristic receiver frequency of the embodiments is further determined in a controlled environment where interfering sources can be controlled or absent and thereby the characteristic receiver frequency will indeed represent a preferred receiver frequency of the broadband RF receiver. The circuitry of the IMD can further be kept simpler since no built-in frequency analyzer with high accuracy is needed in the IMD FIG. 8 is a flow diagram of a method of programming an IMD according to an embodiment. The method starts in step S20 where multiple test messages are transmitted at different radio frequencies within the defined RF band. Alternatively, a broadband signal covering a complete spectrum part of the relevant RF band could be used. However, it is generally preferred to use multiple, i.e. at least two, narrowband or broadband test signals or messages. The receiver sensitivity of the broadband RF receiver at each of the tested radio frequencies is determined in step S21. A next step S22 identifies and determines the characteristic receiver frequency of the broadband RF receiver to correspond to the radio frequency or frequencies of the tested radio frequencies at which the broadband RF receiver has sufficient, preferably maximum, receiver sensitivity. A programming command is transmitted in step S23 to the IMD with the information of the characteristic receiver frequency identified in step S22. The programming command thereby triggers the IMD to store the information in a memory of the IMD.

The above described programming method can be conducted in a controlled test environment in connection with or after the manufacture of the broadband RF receiver and the IMD. The transmitter transmitting the test messages in step S20 could then be accurately placed at a defined distance relative the IMD and the tested frequencies where the receiver sensitivity exceeded a sensitivity threshold could be noted and identified in steps S21 and S22. It could be possible to identify all tested radio frequencies at which the receiver sensitivity exceeded the sensitivity threshold for the defined transmission distance. Alternatively, the radio frequency or frequencies that corresponded to the maximum receiver sensitivity is or are identified in step S22 and employed as characteristic radio frequency of the tested broadband RF receiver.

The embodiments can be used in various scenarios. For instance, during implantation an IMD is interrogated several times in order to check whether it is operating correctly and also to program different programmable parameters and settings. The interrogating communication device benefits from the embodiments since the communication device can then generally be positioned at a longer distance from the IMD when using the characteristic receiver frequency as transmission frequency as compared to a random radio frequency within the RF band. The communication device could thereby be positioned outside of the sterile zone during the implantation operation, reducing the risk of infections in the patient.

Also home monitoring devices that periodically activates and interrogates IMDs would benefit from using the characteristic receiver frequency as its transmission frequency. The home monitoring device can thereby generally set up a communication session over longer communication distances as compared to using randomly selected transmission frequencies. The number of IMD interrogations before the IMD successfully receives the message, such as wakeup call, can also be reduced by the embodiments.

A similar situation also occurs at follow-ups when the IMD patient is visiting his/her physician to check the status of the IMD and interrogate and/or program the IMD.

Figure 9:
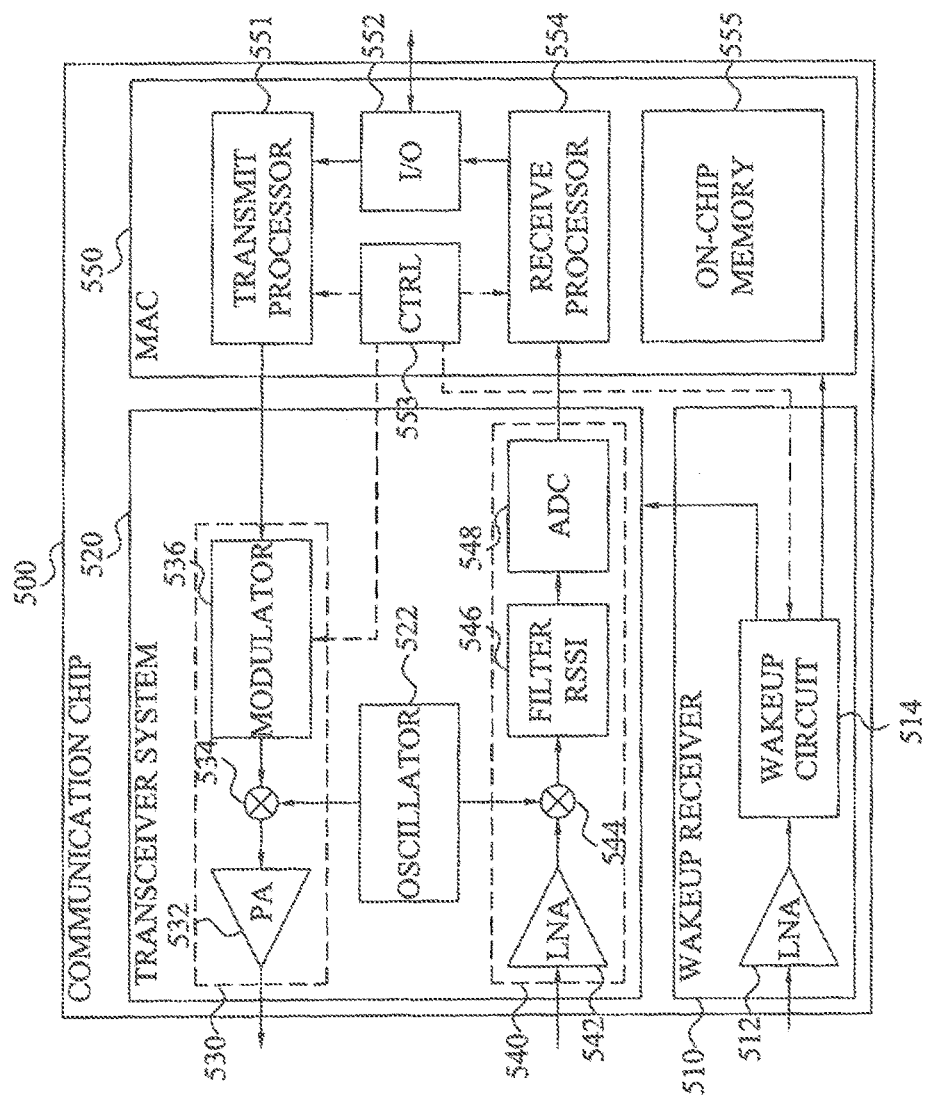
FIG. 9 is a schematic illustration of a communication chip according to an embodiment.

FIG. 9 is a schematic illustration of a communication chip 500 configured to be arranged in an IMD. The communication chip 500 comprises three main units: a transceiver system 520, a wakeup receiver 510 and a media access controller (MAC) 550. The wakeup receiver 510 preferably operates in the previously discussed 2.4000-2.4835 GHz ISM band and the transceiver system 520 preferable operates in the 402-405 MHz MICS band.

The transceiver system 520 in turn comprises a transmitter 530, a receiver 540 and an oscillator 522. The transmitter 530 comprises a modulator 536, a mixer 534 and a power amplifier 532. The modulator 536 converts an input data bit stream from a transmit processor 551 to a data symbol stream. The mixer 534 upconverts the frequency of the data symbol stream to the RF carrier frequency from the oscillator 522.

The receiver 540 amplifies a MICS band signal in a low-noise amplifier 542 and downconverts the carrier frequency to an Intermediate frequency using a mixer 544 and the oscillator 522. A filter 546 suppresses interference and received signal-strength indicator measurements are determined by the block 546. The RSSI measurements are converted to digital bits by an analog-to-digital converter 548 and provided to a receive processor 554.

The MAC 550 comprises the previously mentioned transmit processor 551 and receive processor 554 and an I/O unit 552 that provides the application interface. A control unit 553 controls the operation of the circuitry of the communication chip 500 based on various operation modes stored in an on-chip memory 555

The wakeup receiver 510 is preferably an ultra low power broadband RF receiver. The wakeup receiver 510 comprises a low-noise amplifier 512 and a wakeup circuit 514 that detects and decodes specific messages, such as wakeup calls. If a correct wakeup call is received by the wakeup receiver 510, the transceiver system 520 and the MAC 550 are activated through control signaling from the wakeup circuit 514.

An embodiment of the communication chip 500 stores information of the at least one characteristic receiver frequency of the broadband RF receiver 510 in the on-chip memory 555. In such a case, the controller 553 preferably retrieves this information from the on-chip memory 555 in response to the wakeup receiver 510 receiving a wakeup call and/or in response to the receiver 540 of the transceiver system 520 receiving an explicit request for the information from the non-implantable communication device. The transmit processor 551 then generates a response comprising a notification of the at least one characteristic receiver frequency based on the retrieved information. The response is transmitted by the transmitter 530 to the communication device.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A non-implantable communication device configured to conduct wireless communication with an implantable medical device, IMD, the non-implantable communication device comprising:
   a transmitter configured to transmit a first message to the implantable medical device at a radio frequency selected within a band of radio frequencies;
   a receiver configured to receive a response from the implantable medical device, the response comprises an IMD identifier of the implantable medical device and a notification of at least one characteristic receiver frequency representing a radio frequency within the band of radio frequencies at which a broadband radio frequency receiver of the implantable medical device has sufficient receiver sensitivity;
   a memory;
   a memory controller configured to store the IMD identifier and information of the at least one characteristic receiver frequency in the memory and configured to retrieve the information from the memory based on the IMD identifier and in response to a need to transmit a second message to the implantable medical device; and
   a transmitter controller configured to select a transmission frequency of the transmitter based on the information retrieved from the memory by the memory controller, wherein the transmitter is configured to transmit the second message to the implantable medical device at the transmission frequency selected by the transmitter controller.

2. The non-implantable communication device according to claim 1, wherein the transmitter controller is configured to randomly select a transmission frequency of the transmitter within the band of radio frequencies in response to a need to transmit the first message to the implantable medical device.

3. The non-implantable communication device according to claim 2, wherein the transmitter is configured to i) transmit a first wakeup message to the implantable medical device at the radio frequency selected within the band of radio frequencies in connection with setting up a first communication session and ii) transmit a second wakeup message to the implantable medical device at the transmission frequency selected by the transmitter controller based on the information retrieved by the memory controller in connection with setting up a second, subsequent communication session.

4. The non-implantable communication device according to claim 1, wherein the transmitter controller is configured to control the transmitter to apply frequency hopping within the band of frequencies and control, based on the information retrieved by the memory controller, the transmitter to select a first transmission frequency in a frequency hopping sequence to be equal to the characteristic receiver frequency.

5. A communication control method comprising:
   transmitting a first message to an implantable medical device, IMD, at a radio frequency selected within a band of radio frequencies;
   receiving a response from the implantable medical device, the response comprises an IMD identifier of the implantable medical device and a notification of at least one characteristic receiver frequency representing a radio frequency within the band of radio frequencies at which a broadband radio frequency receiver of the implantable medical device has sufficient receiver sensitivity;
   storing the IMD identifier and information of the at least one characteristic receiver frequency in a memory;
   retrieving the information from the memory based on the IMD identifier in response to a need to transmit a second message to the implantable medical device;
   selecting a transmission frequency based on the information retrieved from the memory; and
   transmitting the second message to the implantable medical device at the selected transmission frequency.

* * * * *